United States Patent
Abhari et al.

(10) Patent No.: US 9,061,951 B2
(45) Date of Patent: *Jun. 23, 2015

(54) BIORENEWABLE NAPHTHA COMPOSITION

(71) Applicant: REG SYNTHETIC FUELS, LLC, Ames, IA (US)

(72) Inventors: Ramin Abhari, Bixby, OK (US); H. Lynn Tomlinson, Leonard, OK (US); Gary Roth, Bristow, OK (US)

(73) Assignee: REG SYNTHETIC FUELS, LLC, Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/050,559

(22) Filed: Oct. 10, 2013

(65) Prior Publication Data

US 2014/0046103 A1 Feb. 13, 2014

Related U.S. Application Data

(63) Continuation of application No. 13/196,768, filed on Aug. 2, 2011, now Pat. No. 8,581,013, which is a continuation-in-part of application No. 12/132,915, filed on Jun. 4, 2008, now abandoned.

(51) Int. Cl.
*C10L 1/00* (2006.01)
*C07C 5/00* (2006.01)
(Continued)

(52) U.S. Cl.
CPC ... *C07C 9/02* (2013.01); *C10G 3/50* (2013.01); *C10G 47/00* (2013.01);
(Continued)

(58) Field of Classification Search
CPC .............. C07C 9/02; C07C 9/22; C07C 9/14; C10G 3/46; C10G 3/50; C10G 47/00; C10G 2300/1014; C10G 2300/1018; C10G 2400/02; C10G 2300/308; C10G 2300/301; Y02E 50/13; C10L 1/06
USPC ............................. 585/14, 250, 804, 828, 12
See application file for complete search history.

(56) References Cited

U.S. PATENT DOCUMENTS

2,093,159 A 9/1937 Schmidt
2,163,563 A 6/1939 Schrauth
(Continued)

FOREIGN PATENT DOCUMENTS

CA 1313200 1/1993
CA 2149685 9/1999
(Continued)

OTHER PUBLICATIONS

Akzo Nobel Catalyst Presentation, Oct. 2003 (63 pages).
(Continued)

*Primary Examiner* — Pamela H Weiss
(74) *Attorney, Agent, or Firm* — Foley & Lardner LLP

(57) ABSTRACT

The present invention generally relates to a method for producing a naphtha product from a renewable feedstock. The method includes hydrotreating the renewable feedstock to produce a hydrotreating unit heavy fraction that includes n-paraffins, and hydrocracking the hydrotreating unit heavy fraction to produce a hydrocracking unit product that includes the naphtha product. The method also includes separating the naphtha fraction and optionally recycling the hydrocracking unit heavy fraction through the hydrocracking unit. The present invention also relates to a biorenewable naphtha product suitable for use as feed stock for steam crackers and catalytic reforming units, and for use as fuel, or fuel blend stock.

19 Claims, 3 Drawing Sheets

(51) Int. Cl.
*C07C 6/00* (2006.01)
*C07C 9/02* (2006.01)
*C10G 3/00* (2006.01)
*C10G 47/00* (2006.01)
*C10L 1/06* (2006.01)
*C07C 9/14* (2006.01)
*C07C 9/22* (2006.01)

(52) U.S. Cl.
CPC ... *C10G 2300/301* (2013.01); *C10G 2300/308* (2013.01); *C10G 2400/02* (2013.01); C10L 1/06 (2013.01); *C10G 3/46* (2013.01); *C10G 2300/1014* (2013.01); *C10G 2300/1018* (2013.01); C07C 9/14 (2013.01); C07C 9/22 (2013.01); *Y02E 50/13* (2013.01)

(56) References Cited

U.S. PATENT DOCUMENTS

| | | | |
|---|---|---|---|
| 2,482,760 | A | 9/1949 | Goebel |
| 2,482,761 | A | 9/1949 | Goebel |
| 2,664,429 | A | 12/1953 | Goebel |
| 2,793,220 | A | 5/1957 | Barrett et al. |
| 2,915,447 | A | 12/1959 | Arabian |
| 3,144,404 | A | 8/1964 | Tyson |
| 3,496,099 | A | 2/1970 | Bridge |
| 4,049,686 | A | 9/1977 | Ringers et al. |
| 4,151,072 | A | 4/1979 | Nowack et al. |
| 4,233,140 | A | 11/1980 | Antonelli et al. |
| 4,252,634 | A | 2/1981 | Khulbe et al. |
| 4,300,009 | A | 11/1981 | Haag et al. |
| 4,431,524 | A | 2/1984 | Norman |
| 4,432,865 | A | 2/1984 | Norman |
| 4,512,878 | A | 4/1985 | Reid et al. |
| 4,554,397 | A | 11/1985 | Stern et al. |
| 4,571,442 | A | 2/1986 | Cosyns et al. |
| 4,698,185 | A | 10/1987 | Dijkstra et al. |
| 4,734,226 | A | 3/1988 | Parker et al. |
| 4,746,420 | A | 5/1988 | Darian et al. |
| 4,937,051 | A | 6/1990 | Graven et al. |
| 4,960,960 | A | 10/1990 | Harrison et al. |
| 4,992,605 | A * | 2/1991 | Craig et al. ............... 585/240 |
| 5,093,535 | A | 3/1992 | Harrison et al. |
| 5,105,015 | A | 4/1992 | Lin et al. |
| 5,135,638 | A | 8/1992 | Miller |
| 5,180,868 | A | 1/1993 | Baker et al. |
| 5,239,096 | A | 8/1993 | Rohdenburg et al. |
| 5,292,428 | A | 3/1994 | Harrison et al. |
| 5,298,639 | A | 3/1994 | Toeneboehn et al. |
| 5,346,724 | A | 9/1994 | Ohgake et al. |
| 5,378,348 | A | 1/1995 | Davis et al. |
| 5,475,160 | A | 12/1995 | Singleton et al. |
| 5,502,077 | A | 3/1996 | Breivik et al. |
| 5,578,090 | A | 11/1996 | Bradin |
| 5,647,226 | A | 7/1997 | Scaringe et al. |
| 5,688,749 | A | 11/1997 | Ibuki et al. |
| 5,705,722 | A | 1/1998 | Monnier et al. |
| 5,851,338 | A | 12/1998 | Pushaw |
| 5,871,618 | A | 2/1999 | Lee et al. |
| 5,877,358 | A | 3/1999 | Garton et al. |
| 5,882,505 | A | 3/1999 | Wittenbrink et al. |
| 5,906,729 | A | 5/1999 | Chou |
| 6,123,835 | A | 9/2000 | Ackerson et al. |
| 6,150,575 | A | 11/2000 | Angevine et al. |
| 6,185,742 | B1 | 2/2001 | Doherty |
| 6,187,903 | B1 | 2/2001 | Elsasser et al. |
| 6,190,535 | B1 | 2/2001 | Kalnes et al. |
| 6,203,695 | B1 | 3/2001 | Harle et al. |
| 6,353,143 | B1 * | 3/2002 | Fang et al. .............. 585/1 |
| 6,399,845 | B1 | 6/2002 | Raulo et al. |
| 6,402,935 | B1 | 6/2002 | Kalnes |
| 6,574,971 | B2 | 6/2003 | Suppes |
| 6,613,404 | B2 | 9/2003 | Johnson |
| 6,638,418 | B1 | 10/2003 | Kalnes et al. |
| 6,660,812 | B2 | 12/2003 | Kuechler et al. |
| 6,787,022 | B1 | 9/2004 | Berlowitz et al. |
| 6,833,064 | B2 | 12/2004 | Berlowitz et al. |
| 6,846,778 | B2 | 1/2005 | Johnson et al. |
| 6,855,410 | B2 | 2/2005 | Buckley |
| 6,858,048 | B1 | 2/2005 | Jimeson et al. |
| 7,232,935 | B2 | 6/2007 | Jakkula et al. |
| 7,288,685 | B2 | 10/2007 | Marker |
| 7,511,181 | B2 | 3/2009 | Petri et al. |
| 7,550,634 | B2 | 6/2009 | Yao et al. |
| 7,691,159 | B2 | 4/2010 | Li |
| 7,718,051 | B2 | 5/2010 | Ginosar et al. |
| 7,754,931 | B2 | 7/2010 | Monnier et al. |
| 7,816,570 | B2 | 10/2010 | Roberts et al. |
| 7,836,722 | B2 | 11/2010 | Magill et al. |
| 7,846,323 | B2 | 12/2010 | Abhari et al. |
| 7,928,273 | B2 | 4/2011 | Bradin |
| 7,968,757 | B2 | 6/2011 | Abhari et al. |
| 7,982,076 | B2 | 7/2011 | Marker et al. |
| 8,003,836 | B2 | 8/2011 | Marker et al. |
| 8,022,258 | B2 | 9/2011 | Myllyoja et al. |
| 8,026,401 | B2 | 9/2011 | Abhari et al. |
| 8,187,344 | B2 | 5/2012 | Jakkula et al. |
| 8,212,094 | B2 | 7/2012 | Myllyoja et al. |
| 8,278,492 | B2 | 10/2012 | Myllyoja et al. |
| 8,581,013 | B2 * | 11/2013 | Abhari et al. ............... 585/14 |
| 2002/0062053 | A1 | 5/2002 | Berlowitz et al. |
| 2004/0055209 | A1 | 3/2004 | Jakkula et al. |
| 2004/0067856 | A1 | 4/2004 | Johnson et al. |
| 2004/0167355 | A1 * | 8/2004 | Abazajian ............... 562/93 |
| 2004/0170806 | A1 | 9/2004 | Hittle et al. |
| 2004/0230085 | A1 | 11/2004 | Jakkula et al. |
| 2005/0150815 | A1 | 7/2005 | Johnson et al. |
| 2006/0006098 | A1 | 1/2006 | Espinoza et al. |
| 2006/0100473 | A1 | 5/2006 | Grootjans et al. |
| 2006/0161032 | A1 | 7/2006 | Murzin et al. |
| 2006/0186020 | A1 | 8/2006 | Gomes |
| 2006/0199984 | A1 | 9/2006 | Kuechler et al. |
| 2006/0199988 | A1 | 9/2006 | Kowalik et al. |
| 2006/0207166 | A1 | 9/2006 | Herskowitz et al. |
| 2006/0264684 | A1 | 11/2006 | Petri et al. |
| 2007/0006523 | A1 | 1/2007 | Myllyoja et al. |
| 2007/0010682 | A1 | 1/2007 | Myllyoja et al. |
| 2007/0026012 | A1 | 2/2007 | DeLisa et al. |
| 2007/0131579 | A1 | 6/2007 | Koivusalmi et al. |
| 2007/0135669 | A1 | 6/2007 | Koivusalmi et al. |
| 2007/0161832 | A1 | 7/2007 | Myllyoja et al. |
| 2007/0170091 | A1 | 7/2007 | Monnier et al. |
| 2007/0260102 | A1 * | 11/2007 | Duarte Santiago et al. .. 585/733 |
| 2009/0077866 | A1 | 3/2009 | Kalnes et al. |
| 2012/0157726 | A1 | 6/2012 | Vauk et al. |

FOREIGN PATENT DOCUMENTS

| | | |
|---|---|---|
| CZ | 283575 | 5/1998 |
| DE | 41 16 905 | 8/1992 |
| EP | 0 412 785 | 2/1991 |
| EP | 0 794 241 | 3/1997 |
| EP | 1396531 | 3/2004 |
| EP | 1 728 844 | 12/2006 |
| EP | 1 741 768 | 1/2007 |
| FI | 72435 | 2/1987 |
| FI | 73367 | 6/1987 |
| FI | 89073 | 4/1993 |
| FI | 95391 | 1/1996 |
| FR | 2607803 | 6/1988 |
| GB | 2 090 611 | 7/1982 |
| IE | 921671 | 12/1995 |
| JP | 59-108088 | 6/1984 |
| SE | 9700149 | 8/1997 |
| SE | 520633 | 8/2003 |
| WO | WO-00/11117 | 3/2000 |
| WO | WO-00/29512 | 5/2000 |
| WO | WO-01/49812 | 7/2001 |
| WO | WO-03/022960 | 3/2003 |
| WO | WO-2004/026161 | 4/2004 |
| WO | WO-2004/104142 | 12/2004 |
| WO | WO-2005/026297 | 3/2005 |
| WO | WO-2006/100584 | 9/2006 |

(56) References Cited

FOREIGN PATENT DOCUMENTS

| WO | WO-2007/003708 A1 | 1/2007 |
|----|-------------------|--------|
| WO | WO-2007/063874 | 6/2007 |
| WO | WO-2007/068795 | 6/2007 |
| WO | WO-2008/027699 | 3/2008 |
| WO | WO-2008/054442 | 5/2008 |
| WO | WO-2008/058664 | 5/2008 |
| WO | WO-2008/067627 | 6/2008 |
| WO | WO-2009/085686 | 7/2009 |
| WO | WO-2009/117337 | 9/2009 |
| WO | WO-2009/151692 | 12/2009 |

OTHER PUBLICATIONS

Alencar, J.W., et al., Pyrolysis of Tropical Vegetable Oils, J. Agric. Food Chem., vol. 31, 1983, pp. 1268-1270.
Arca, M., et al., Evidence Contrary to the Accepted Diels-Alder Mechanism in the Thermal Modification of Vegetable Oils, J. Am. Oil Chem. Soc., 89 (2012), pp. 987-994.
Bradley, T.F., et al., Drying Oils and Resins, Ind. & Eng. Chem., vol. 32, No. 6, 1940, pp. 802-809.
Duncan, D.P. in "Naval Stores," Zinkel, et al., Editors, Pulp Chemicals Association, New York, 1989, pp. 388-389.
Formo, M.W., Ester Reactions of Fatty Materials, J. Am. Oil Chem. Soc., vol. 31, 1954, pp. 548-559.
Leonard, E.C., Polymerization—Dimer Acids, J. Am. Oil Chem. Soc., vol. 56, 1979, pp. 782A-785A.
Nawar, W.W., Thermal Degradation of Lipids. A Review, J. Agr. Food Chem, vol. 17, No. 1, 1969, pp. 18-21.
Paschke, R.F. et al., Dimer Acid Structures. The Thermal Dimer of Methyl 10-trans, 12-trans, Linoleate, J. Am. Oil Chem. Soc., vol. 41, 1964, pp. 723-727.
Paschke, R.F., et al., Thermal Polymerization of Unsaturated Fatty Esters Normal Methyl Linoleate, J. Am. Oil Chem. Soc., 1949, pp. 278-283.
Petrocelli, F.P. et al., Modeling Lignin Liquefaction—Catalytic Hydroprocessing of Lignin-Related Methoxyphenols and Interaromatic Unit Linkages, Fuel Sci. & Tech., 5(1), 1987, pp. 25-62.
Senol, et al., Hydrodeoxygenation of aliphatic esters on sulphided NiMo/ γ-Al2O3 and CoMo/ γ-Al2O3 catalyst: The effect of water, Catalysis Today, 106 (2005), pp. 186-189.
Senol, et al., Hydrodeoxygenation of methyl esters on sulphided NiMo/ γ-Al2O3 and CoMo/ γ-Al2O3 catalysts, Catalysis Today, 100 (2005), pp. 331-335.
Venkatachalam, et al., Kinetics of Oligomerization of Methyl Ester of Dehydrated Castor Oil Fatty Acid over Molybdenum Oxide on Silica-Alumina Catalyst in Comparison with the Thermal Oligomerization Process, J. Poly. Sci. Poly. Chem. Ed., vol. 22, 1984, pp. 3805-3814.
Abhari et al., "New Routes to Ethylene," EEPC Seminar in Berlin, Germany, Oct. 20-22, 2010, pp. 1-38.
Ali et al., "Fuel Properties of Tallow and Soybean Oil Esters," JAOCS, 1995, vol. 72, No. 12.
Ali, et al., "Mineral Composition, Quality and Physico-chemical Parameters of the Local Tallow of Pakistan," Pakistan Journal of Nutrition, 7(5): 717-720, 2008.
American Petroleum Institute, Properties of Hydrocarbons of High Molecular Weight Synthesized by Research Project 42 of the American Petroleum Institute (1967).
Antoniassi, R. et al, "Pretreatment of Corn Oil for Physical Refining," JAOCS, vol. 75, No. 10, 1998, pp. 1411-1415.
Arroyo et al., "Hydrocracking and isomerization of n-paraffin mixtures and a hydrotreated gasoil on Pt/ZSM-22: confirmation of pore mouth and key013lock catalysis in liquid phase," Applied Catalysis A: General 192, 2000, pp. 9-22.
ASTM International, "Standard Specification for Diesel Fuel Oil", Designation: D975-12, printed Nov. 9, 2012, 26 pages.
ASTM International, Designation: D6751-11b, "Standard Specification for Biodiesel Fuel Blend Stock (B100) for Middle Distillate Fuels," Jul. 2011, pp. 1083-1091.

B.B. He and J. Van Gerpen "Biodiesel Quality Affected by Sulfur Content Originated by Different Feedstocks and a Database for the Same" Final Report KLK432 N08-04, National Institute for Advanced Transportation Technology, University of Idaho (Feb. 2008).
Batts et al., "A Literature Review on Fuel Stability Studies with Particular Emphasis on Diesel Oil", Energy & Fuels, 1991, vol. 5, pp. 2-21.
Beare-Rogers, J. et al, "Lexicon of Lipid Nutrition," Pure and Applied Chemistry, vol. 73, No. 4, 2001, pp. 685-744.
Bell, et al., "Biodiesel," TEAM Report for Imperial Oil, Queen's University, Kingston, Ontario, Apr. 2007. (106 pages).
Bergerioux, C. et al, "Determination of Trace Element Pathways in a Petroleum Distillation Unit by Instrumental Neutron Activation Analysis," Journal of Radioanalytical Chemistry, vol. 54, No. 1-2,1979, pp. 255-265.
Burch et al., "Melting-Point Models of Alkanes", J. Chem. Eng. Data 2004, 49, 858-863.
Canada Centre for Mineral and Energy Technology, "New Process Yields Cleaner Diesel", Canmet'95: New Directions, 1995, p. 14.
Canakci et al., "Biodiesel Production from Oils and Fats with High Free Fatty Acids", Transactions of the ASAE, 2001, vol. 44(6), pp. 1429-1436.
CanmetENERGY's SuperCetane Technology, Natural Resources Canada, http://cetcvareness.nrcan.gc.ca/eng/industrialprocesses/industrialenergysystems, Nov. 2008, Accessed Jul. 19, 2013 (4 pages).
Clements, L.D., "Blending Rules for Formulating Biodiesel Fluid.", Proceedings of the Third Liquid Fuels Conference, Sep. 15-17, 1996, pp. 44-53.
Cmolik et al., "Effects of plant-scale alkali refining and physical refining on the quality of rapeseed oil", Eur. J. Lipod Sci. Technol. 2000, 15-22.
Connor, et al., "Hydrogenolysis of Oxygenated Organic Compounds," J. Am. Chem. Soc., 54(12), 1932, pp. 4678-4690.
Cooper et al., "Production of Swedish Class I Diesel Using Dual-Stage Process", Catalytic Hydroprocessing of Petroleum and Distillates, based on Proceedings of the AIChE Spring National Meeting, Houston, Texas, Mar. 28-Apr. 1, 1993, 279-290.
Corma, et al., "Transformation of Alkanes on Solid Acid and Bifunctional Catalysts", Catalytic Activation and Functionalisation of Light Alkanes: Advances and Challenges, Editors E.G. Derouane et al., 1998, Netherlands: Kluwer Academic Publishers, vol. 44, pp. 35-74.
Craig, et al., "A Marketing Survey of Worldwide Potential for Use of Vegetable Oil Conversion Products in Diesel Fuel," Saskatchewan Research Council, Oct. 1989 (182 pages).
Criterion, "Technical Bulletin: Criterion* Hydrotreating Catalyst In-Situ Presulphiding Guidelines—Liquid Phase (Preferred method)—Gase Phase (alternative method)" Criterion Catalysts, Aug. 1998, 1-9.
Declaration of Jaques Monnier under 37 C.F.R. 1.132, dated Jan. 7, 2010, filed in U.S. Appl. No. 11/234,175.
Deem, A.G. et al, "Catalytic Poisoning in Liquid-Phase Hydrogenation," Industrial and Engineering Chemistry, vol. 33, No. 11, Nov. 1941, pp. 1373-1376.
Del Gallo et. al. "Comparison of the Effects of Nitrogen Poisoning on Molybdenum Oxycarbide and Pt/B-Zeolite Catalysts in the Isomerization of n-Heptane," Ind. Eng. Chem. Res., 1996, vol. 35, No. 10, pp. 3302-3310.
Derrien et al., "The IFP Selective Hydrogenation Process", Chemical Engineering Process, vol. 70, No. 1, Jan. 1974, 74-80.
Dynamic Fuels, "About", http://www.dynamicfuelsllc.com/. Accessed Nov. 12, 2012, 8 pages.
Dynamic Fuels, "Compare", http://www.dynamicfuelsllc.com/. Accessed Nov. 12, 2012, 7 pages.
Dynamic Fuels, "Frequently Ask Questions," http://dynamicfuelsllc.com/wpnews/frequently-ask-questions/, Accessed Nov. 12, 2012, 4 pages.
Edgar et al., "Analysis is key to hydrotreater troubleshooting", Oil & Gas Journal, vol. 82, issue 23, Jun. 4, 1984, 67-70.
Elliott, et al., "Hydrodeoxygenation of Wood-Derived Liquids to Produce Hydrocarbon Fuels," Proceedings of the 20th Intersociety Energy Conversion Engineering Conf., vol. 1 of 3, 1985. (9 pages).

(56) References Cited

OTHER PUBLICATIONS

Erickson et al., "Soybean Oil Modern Processing and Utilization", American Soybean Association, 1990, 20 pages.
Extended European Search Report issued for European Application No. 09759070.7 dated Nov. 5, 2012.
Feng et al., "Chemical Composition of Tall-Oil Based Cetane Enhancer for Diesel Fuels", First Biomass Conference of The Americas: Energy, Environment, Agriculture, and Industry, Aug. 30-Sep. 2, 1993. 14 pages.
Ferrari, M. et al. "Hydrotreatment and Hydrocracking of Oil Fractions," Elsevier Science, pp. 85-95, 1999.
File History of U.S. Appl. No. 08/269,090 to Monnier et al., (filed Jun. 30, 1994) (abandoned).
File History of U.S. Appl. No. 08/517,421 to Monnier et al., (filed Aug. 21, 1995) (continuation-in-part).
Filho et al., Catalytic Conversion of *Hevea brasiliensis* and *Virola sebifera* Oils to Hydrocarbon Fuels, JAOCS, vol. 69, No. 3, Mar. 1992, 266-271.
Final Office Action in U.S. Appl. No. 13/196,768 dtd Aug. 26, 2013.
Final Substantive Examination Report issued for Singapore application No. 201008935-7 dated Feb. 1, 2013.
First Action Interview Office Action on U.S. Appl. No. 13/742,255 DTD Jun. 6, 2013.
First Action Interview Pilot Program Pre-Interview Communication issued for U.S. Appl. No. 13/742,255 mailed Apr. 12, 2013.
Food Fats and Oils, Inst. of Shortening and Edible Oils, 335-354 (9th Ed. 2006).
Galeana et al., "Thermodynamics of Wax Precipitation in Petroleum Mixtures," AIChE Journal, 1996, vol. 42, No. 1, pp. 239-248.
Galperin, "Hydroisomerization of N-decane in the presence of sulfur and nitrogen compounds," Applied Catalysis A: General, 209, 2001 pp. 257-268.
Garrido et al., "Concentrations of Metal in vegetable edible oils", Food Chemistry, vol. 50, 1994, 237-243.
Ghosh, et al., "Detailed Composition-Based Model for Predicting the Cetane Number of Diesel Fuels," Ind. Eng. Chem. Res. 2006, 45, 346-351.
Goering et al., "Fuel Properties of Eleven Vegetable Oils," Transactions of the ASAE, 1982, pp. 1472-1477, 1483.
Goodfellow, J., "Animal Fat-Based Biodiesel: Explore Its Untapped Potential," Biodiesel Magazine, Feb. 10, 2009 (1 page).
Goodfellow, J., "Biofuel Production From Animal Fats: A North American Perspective," Sanimax Energy (23 pages).
Goodrum et al., "Rheological Characterization of Yellow Grease and Poultry Fat," JAOCS, 2002, vol. 79, No. 10, pp. 961-964.
Gorshteyn, et al., "ExxonMobil Catalytic Dewaxing—A Commercial Proven Technology," Paper presented at the 2nd Russian Refining Technology Conference, Moscow, Sep. 26-27, 2002, 13 pages.
Gosselink, et al., "Mild Hydrotracking: Coping with Catalyst Deactivation," 34 Catalyst Deactivation, 279-287 (1987).
Groschen, R., "Overview of: The Feasibility of Biodiesel from Waste/Recycled Greases and Animal Fats", Marketing Services Division, Minnesota Department of Agriculture, Oct. 2002, 28 pages.
Gunstone, F.D., et al., "The Lipid Handbook," Ch. 3 & 6, Chapman & Hall, Second Edition, 1994.
Gusmao et al., "Utilization of Vegetable Oils as an Alternative Source for Diesel-Type Fuel," Catalysis Today, 5, 1989, pp. 533-544.
Haas, M., "Animal Fats," Bailey's Industrial Oil and Fat Products, 6th Ed., vol. 1: Edible Oil and Fat Products: Chemistry, Properties, and Health Effects, 2005, pp. 161-212.
Hammami, et al., "Cloud Points: Can We Measure or Model Them?" Petroleum Science and Technology, vol. 21, Nos. 3 & 4, 2003, pp. 345-358.
Held, et al., "Production of Hydrocarbons from Biomass," Energy from Biomass: 3rd E.C. Conference, International Conference on Biomass, Venice, 1985 (7 pages).
Herrera et al., "Catalyst Selection for Hydrotreating Diesel Fuel from Residue Hydrocracking", ACS Preprints, 1992, vol. 37, No. 4, pp. 1855-1863.
Hill, C., An Introduction to Chemical Engineering Kinetics & Reactor Design, John Wiley & Sons, Inc., 1977, pp. 349-380, 382-387.
Holmgren, et al., "New Developments in Renewable Fuels Offer More Choices", Hydrocarbon Processing, Sep. 2007, pp. 67-72.
Iki, et al., "Applicability of Hydrogenated Palm Oil for Automotive Fuels", 16th Saudi Arabia-Japen Joint Symposium, Dhahran, Saudi Arabia, Nov. 5-6, 2006, 10 pages.
Irwin, R.J., et al. 1997. "Environmental Contaminants Encyclopedia," Diesel Oil Entry. National Park Service, Water Resources Division, Fort Collins, Colorado. (Distributed within the Federal Government as an Electronic Document).
J. Johnson, et al. "Emissions from Fischer-Tropsch Diesel Fuels" SAE Technical Paper 2001-01-3518 (published Sep. 24, 2001) ("SAE 2001").
Kalines, et al.; U.S. Appl. No. 60/973,788, entitled "Production of Diesel Fuel from Biorenewable Feedstocks", filed Sep. 9, 2007.
Kent, J., "Table 8.2", Riegel's Handbook of Industrial Chemistry, 9th Edition, 1992, pp. 278-279.
Kirk-Othmer, "Gravity Concentration to Hydrogen Energy", Encyclopedia of Chemical Technology, Third Edition, vol. 12, Copyright 1980 by John Wiley & Sons, Inc., 931-937.
Klimisch et al., "Paraffinic Naphthas", American Petroleum Institute, May 20, 2003, 41 pages.
Kriz, et al., "Catalysts for the Isomerization of C7 Paraffins," Ind. Eng. Chem. Res., 1998, 37:4560-4569.
Kubicka, et al., "Transformation of Plant Oils to Hydrocarbons," APROCHEM 2007, 1149-1155, Apr. 16-18, 2007.
L. Rantanen, R. Linnaila, P. Aakko, and T. Harju "NExBTL—Biodiesel Fuel of the Next Generation" SAE Technical Paper 2005-01-3771 (published Oct. 24, 2005).
L.G. Huve "Shell Global Solutions Dewaxing Technologies & Catalysts Current Status" pp. 1-13., 2007.
Latondress, E.G., "Refining, Bleaching and Hydrogenating Meat Fats," JAOCS, vol. 62, No. 4, 1985, pp. 812-815.
Laurent, et al., "Study of the hydrodeoxygenation of carbonyl, carboxylic and guaiacyl groups over sulfided CoMo/ γ-Al2O3 and NiMo/ γ-Al2O3 catalyst," App. Catal. A 109, pp. 97-115 (1994).
Laurent, et al., "Study of the hydrodeoxygenation of carbonyl, carboxylic and guaiacyl groups over sulfided CoMo/ γ-Al2O3 and NiMo/ γ-Al2O3 catalyst," App. Catal. A 109, pp. 77-96 (1994).
Leng, et al., "Catalytic Conversion of Palm Oil to Fuels and Chemicals," The Canadian Journal of Chemical Engineering, vol. 77, Feb. 1999, pp. 156-162.
Levenspiel, O., Chemical Reaction Engineering, Third Edition, John Wiley & Sons, Inc., 1999, pp. 207-239.
Lewis, R.J., Hawley's Condensed Chemical Dictionary, 12th Edition, 1993, p. 907.
Long et al., "Noble Metal (Pt, Rh, Pd) Promoted Fe-ZSM-5 for Selective Catalytic Oxidation of Ammonia to N2 at Low Temperatures", Catalysis Letters, Mar. 2002, vol. 78, Nos. 1-4, pp. 353-357.
Long, et al., "A Simple Test to Detect Chlorophyll in Tallow," Presented before the 8th Annual Fall Meeting—A.O.C.S., Oil & Soap, 1935. (2 pages).
MacDonald, "Fuel From Fats," enerG Alternative Sources Magazine, Sep./Oct. 2011, 4 pages.
Mag, T., "Canola Seed and Oil Processing", Canola Council of Canada, 1994, 6 pages.
Mansfield Fuels, "Norfolk Southern Pens Deal with Dynamic Fuels and Mansfield Oil", http://www.mansfieldoil.com/latest-news-a-press/524-norfolk-southern-pens-deal-with-dynamic-fueis-and-mansfield-oil.html, Accessed Nov. 12, 2012, 2 pages.
Marker, T.L., "Opportunities for Biorenewables in Oil Refineries Final Technical Report," submitted to U.S. Department of Energy, Apr. 2005, 60 pages.
Miller, "Studies on Wax Isomerization for Lubes and Fuels, Zeolited and Related Microporous Materials: State of the Art in 1994," Studies in Surface Science and Catalysts, 1994, vol. 84, pp. 2319-2326.
Mirante et al., "Cloud point prediction of fuels and fuel blends," Fluid Phase Equilibria 180, 2001, pp. 247-255.
Moyse, "Graded Catalyst Systems to Combat Bed-Fouling Problems", Haldor Topsoe, Inc. 1996, 16 pages.
Neste Oil, NExBTL Renewable Synthetic Diesel, Cal Hodge handout presented at Climate Action Team Technology Symposium, Sacra-

(56) References Cited

OTHER PUBLICATIONS mento, California, Jun. 27-28, 2006, available at http://www.climatechange.ca.gov/events/2006-06-27 28_symposium/presentations/ (last modified May 7, 2008).
Non-Final Office Action issued in U.S. Appl. No. 13/196,768 mailed Apr. 18, 2013.
Notice of Allowance in U.S. Appl. No. 13/196,768 dtd Sep. 19, 2013.
Notice of Allowance in U.S. Appl. No. 13/742,255 dtd Aug. 14, 2013.
PCT Preliminary Report; PCT/US2009/045404; International Bureau; dated Dec. 16, 2010; 9 pages.
Plantenga et al., "Specialized guard-bed technology can improve resid unit operation", Oil & Gas Journal, Oct. 21, 1991, 74-78.
Pope et al., "A Study of Catalyst Formulations for Isomerization of C7 Hydrocarbons", Applied Catalysis A: General 233, 2002, pp. 45-62.
Prakash, "A Critical Review of Biodiesel as a Transportation Fuel in Canada", Mar. 25, 1998, 163 pages.
Proctor & Gamble, "Better Rendering, A Manual Prepared by Proctor & Gamble", 2nd Ed., 1967, pp. ix-xi, 1-21.
Properties of Isononane—High Quality Chemical Properties, Accessed at http://chemeo.com/cid/73-453-8 on Aug. 23, 2013 (2 pages).
Przybylski,R., "Canola Oil: Physical and Chemical Properties", Canola Council of Canada, 1998, 12 pages.
Rahimi et al., "Effect of Hydrotreating on the Stability of Synthetic Crude from Western Canada," Symposium on Stability and Oxidation Chemistry of Fuels, Dallas, Spring 1998, ACS Fuels43(1), pp. 13-17; Available for download athttp://web.anl.gov/PCS/acsfuel/preprint%20archive/43_1_DALLAS_03-98.htm.
Sandler, S., "Chemical and Engineering Thermodynamics," at 1-3, 324-33, 598-603 (3rd Ed. 1999).
Sanford et al., "Improved Catalyst Loading Reduces Guard Reactor Fouling", Oil & Gas Journal, Dec. 19, 1988, pp. 35-41.
Santana, et al., "Evaluation of Different Reaction Strategies for the Improvement of Cetane Number in Diesel Fuels," Fuel 85: 643-656 (2006).
Satterfield, C.N., Heterogeneous Catalysis in Industrial Practice, 2nd Edition, Sections 9.8-9.11, McGraw-Hill, Inc., NY (1991), pp. 375-389.
Semjkal, et al., "Thermodynamic balance in reaction system of total vegetable oil hydrogenation", Chemical Engineering Journal 146 (2009) 155-160.
SG Written Opinion; Application No. 201008935-7; Danish Patent and Trademark Office; dated Sep. 1, 2012; 18 pages.
Sharma, S.D., et al.; "Latent Heat Storage Materials and Systems: A Review"; International Journal of Green Energy; 2:1-56; 2005.
Sharp, D.W.A., The Penguin Dictionary of Chemistry, Second Edition, 1990, pp. 207, 263, 432, 433.
Simacek, et al., "Hydroprocessed rapeseed oil as a source of hydrocarbon-based biodiesel", Fuel 88, 2009, 456-460.
Sixth Canadian Bioenergy R&D Seminar, Richmond, B.C., 1987 (19 pages).
Smith, et al., "Introduction to Chemical Engineering Thermodynamics," 5th Ed., 1996, pp. 526-531.
Song, et al., Temperature Programmed Retention Indices for GC and GC-MS of Hydrocarbon Fuels and Simulated Distillation GC of Heavy Oils, Analytical Advances for Hydrocarbon Research, 147-210, 2003.
Soveran et al., "The Effect on Diesel Engine Emissions with High Cetane Additives From Biomass Oils," Proc. American Chemical Society (Division of Fuel Chemistry) Meeting San Francisco, CA, Apr. 1992, pp. 74-85.
Spataru, "AGTANE (AGricultural ceTANE): An Economically Viable Bioenergy Product for Compression Ignited Engines", Fuel Chemistry Division Preprints, 2002, vol. 47(1), p. 365.
Spataru, "Is There a Future for Yellow Grease as a Fuel Additive?," Render, Feb. 2001, pp. 12-14.
Spataru, et al., "AGTANE (AGricultural ceTANE): An economically viable bioenergy product for compression ignited engines," 5th International Biomass Conference of the Americas Sep. 21, 2001, 2 pages.

SRI, "Sample Analyses Final Report" Southwest Research Institute, Oct. 31, 2008, 2 pps.
Standard Methods for the Analysis of Oils, Fats and Derivatives, 6th Ed., Part 1, pp. 96-108 (Pergamon Press 1979).
Stork, W.H.J., "Molecules, catalysts and reactors in hydroprocessing of oil fractions", Hydrotreatment and Hydrocracking of oil fractions, 1997 Elsevier Science B.V., 41-67.
Stumborg et al., "Hydroprocessed Vegetable Oils for Diesel Fuel Improvement." Bioresources Technology, 1996, vol. 56, pp. 13-18.
Stumborg, et al., "Catalytic Conversion of Vegetable Oils to Diesel Additives," Energy from Biomass and Wastes XVI, pp. 721-738, 1993.
Syntroleum webpage, "Bio-Synfining—Dynamic Fuels Plant"; http://www.b2i.us/profiles/investor/fullpage.asp?BzID=2029&to=cp&Nav=O&LangID=1&s=0&ID=11923, Accessed Nov. 21, 2012, 4 pages.
Table 4a. U.S. Crude Oil and Liquid Fuels Supply, Consumption and Inventories, Dec. 2012, 1 pp.
Taylor et al., Modern Advanced Control Pays Back Rapidly, Hydrocarbon Processing, Sep. 2000 issue, pp. 47-50.
Tempier, et al., "Identifying Environmentally Preferable Uses for Biomass Resources," Ch. 4, (Mar. 31, 2004).
Tyson et al., "Biomass Oil Analysis: Research needs and Recommendations," NREL Technical Report, Jun. 2004, 116 pages.
U.S. Dept. of Agriculture—Oilseeds: World Markets and Trade, "Soybean Oil and Palm Oil Account for an Increasing Share of Word Vegetable Oil Consumption", (2003), 27 pages.
U.S. Natural Gas Wellhead Price data and graph from U.S. Energy Information Administration, released Nov. 30, 2012, 1 pp; Available for download at http://www.eia.gov/dnav/ng/ng_pri_sum_dcu_nus_m.htm.
Vajo, et al., "Steady-State Decomposition of Ammonia on the Pt(110)-(1×2) Surface", The Journal of Physical Chemistry, 1986, vol. 90, No. 24, pp. 6531-6535.
Widmor, et al., "Prediction of the Freeze Point Temperature of Jet Fuel Using a Thermodynamic Model," Petroleum Chem. Div. Preprints, 47(3): 329-242 (2002).
Wong et al., "Conversion of Vegetable Oils and Animal Fats Into Paraffinic Cetane Enhancers for Diesel Fuels," Second Biomass Conference of the Americas: Energy, Environment, Agriculture, and Industry, 1995, pp. 901-910.
Wong, A., Arbo-Tane, The Green Diesel Fuel, Naval Stores Review 14-15 (Jul./Aug. 1991).
Wong, A., et al.; "Technical and Economic Aspects of Manufacturing Cetane-Enhanced Diesel Fuel from Canola Oil"; Bio-Oils Symposium; Saskatoon, Saskatchewan, Canada; Mar. 2-3, 1994.
Wong, et al., Bio-Based Cetane Enhancer for Diesel Fuels, BioEnergy 1998: Great Lakes Regional Biomass Energy Program. (12 pages).
Wong, Tall Oil-Based Cetane Enhancer for Diesel Fuel, in 79th Annual Meeting, Technical Section, Canadian Pulp and Paper Association, Preprints "A", A313-A318, held Jan. 26-27, 1993.
Communication pursuant to Article 94(3) EPC issued in EP Application No. 09759070.7 dtd Oct. 23, 2013 (8 pages).
Huber, et al., "Synergies between Bio- and Oil Refineries for the Production of Fuels from Biomass," Agnew. Chem. Int. Ed. 2007, 46, 7184-7201.
Affens, et al., "Effect of Composition on Freezing Points of Model Hydrocarbon Fuels," presented before the Division of Fuel Chemistry, American Chemical Society, New York, Aug. 1981, 9 pages, available at https://web.anl.gov/PCS/acsfuel/preprint%20archive/Files/26_3_NEW%20YORK_08-81_0178.pdf (subsequently published in Fuel, 63(4), Apr. 1984, pp. 543-547).
B. Lee, et al., "Bioremediation and Ecotoxicity of Drilling Fluids Used for Land-based Drilling," AADE Technical Conference, Houston, Apr. 2002, pp. 1-12.
Chaurasia, et al., "Quantitation of Fatty Acids and Hydroxy Fatty Acids by Gas Chromatography/Mass Spectrometry. Predictively Useful Correlations of Relative Response Factors with Empirical Formula," Journal of Mass Spectrometry, 30:1018-1022 (1995).
Chevron Philips Chemical Co., "Synfluid PAO 2 cSt Material Safety Data Sheet," revised Aug. 2005, accessed at http://www.leco.com/component/edocman/?task=document.viewdoc&id=592, 8 pages.

(56) References Cited

OTHER PUBLICATIONS

Communication dated May 26, 2014 from the Technische Informationsbibliothek und Universitätsbibliothek Hannover, Germany (English translation included -3 pages).
D.V. Hale, et al, "Phase Change Materials Handbook," NASA Contractor Report 61363, Sep. 1971, 204 pages.
European Committee for Standardization (CEN), "Automotive fuels—Paraffinic diesel from synthesis or hydrotreatment—Requirements and test methods," TC WI WS038: 2009 (E), 10 pages.
European Food Safety Authority, "Scientific Opinion on the re-evaluation of candelilla wax (E 902) as a food additive," EFSA Journal 2012;10(11): 2946 (published Jan. 28, 2013), 27 pages.
European Standard EN 590:2004, "Automotive Fuels—Diesel—Requirements and Test Methods," Swedish Standards Institute, 2004, English version, available at http://www.repsol.com/imagenes/es_gl/EN%20590_04_93548_tcm10-67163.pdf, 13 pages.
Filter Manufacturers Council, "Solving Winter Diesel Fuel / Fuel Filter Problems," Technical Service Bulletin 91-1R3, 1991 (Revised 2006), available at http://www.hastingsfilter.com/Literature/TSB/91-1R3.pdf, 2 pages.
Göröcs, et al., "The Determination of GC-MS Relative Molar Responses of Some n-Alkanes and their Halogenated Analogs," Journal of Chromatographic Science, 51:138-145 (2013).
Griesbaum, et al., "Hydrocarbons," Ullmann's Encyclopedia of Industrial Chemistry, 2000, 61 pages.
Iki, et al., "Vegetable Oil Hydrogenating Process for Automotive Fuel," SAE Technical Paper, Jul. 23, 2007, pp. 1871-1876.
Kirk-Othmer, "Concise Encyclopedia of Chemical Technology," John Wiley & Sons, Inc., New York NY, pp. 367-369, (1985).
Lange, N.A., "Lange's Handbook of Chemistry," (Ed. Dean, J.A.), Thirteenth Edition, 1985, pp. 7.375 & 7.626.
Non-Final Office Action in U.S. Appl. No. 13/197,542 dtd May 12, 2014 (10 pages).
Non-Final Office Action in U.S. Appl. No. 14/458,119 dtd Dec. 22, 2014 (11 pages).
Sinha, et al., "Hydroisomerization of n-Alkanes over Pt-SAPO-11 and Pt-SAPO-31 Synthesized from Aqueous and Nonaqueous Media," Ind. Eng. Chem. Res., 1998, 37 (6), pp. 2208-2214.
Tong, et al., "Flame Ionization Detector Response Factors for Compound Classes in Quantitative Analysis of Complex Organic Mixtures," Anal. Chem., 56:2124-2128 (1984).

\* cited by examiner

BIORENEWABLE NAPHTHA COMPOSITION

CROSS-REFERENCE TO RELATED PATENT APPLICATIONS

This application is a Continuation of U.S. Ser. No. 13/196,768, filed Aug. 2, 2011, which is a Continuation-In-Part of U.S. application Ser. No. 12/132,915, filed Jun. 4, 2008, both of which are incorporated herein by reference, in their entireties, for any and all purposes.

FIELD OF THE INVENTION

The present invention generally relates to a method for producing hydrocarbons from biomass. Specifically, the present invention relates to converting naturally occurring triglycerides and fatty acids to a composition including naphtha boiling range hydrocarbons. The present invention also relates to the resultant biorenewable naphtha product, whereby the naphtha is used as chemical feed stock, fuel, fuel blend stock, or solvent.

BACKGROUND OF THE INVENTION

The term "green chemistry" has been used to describe synthesis of chemicals from biorenewable feed stocks. It is considered a sustainable alternative to petroleum-based chemistry, and may mitigate the effect of high oil prices. One of the challenges facing transition to a green chemical industry is that the existing production facilities and infrastructure are designed around hydrocarbon feed stocks. For example, the building blocks of the chemical industry, olefins and BTX aromatics (benzene, toluene, and xylene), are produced in steam crackers (also referred to as ethylene crackers) and catalytic reformers that run on light hydrocarbons. Synthesis gas, or syngas for short, is another chemical building block. Syngas is a mixture of carbon monoxide and hydrogen and can be produced by steam reforming of light hydrocarbons. Naphtha is a $C_5$-$C_9$ hydrocarbon cut that is commonly used as the feedstock for both catalytic reformers and steam crackers. It may also be used as feed for steam reforming units for production of syngas.

In particular, paraffinic naphtha is considered a highly desired feed for steam crackers due to its high ethylene and propylene yields. Production of naphtha from biorenewable sources would enable transition to a green chemical industry without the need to develop new chemistries and build new production facilities.

Naphtha is also a common industrial solvent. Extraction of lipids from seeds (e.g. soybean oil) uses n-hexane from petroleum naphtha. However virgin naphtha distilled from crude oil typically contains 2.5% to 5.0% by weight benzene, a well-known carcinogen. As such, multiple and costly purification steps (e.g. solvent extraction and super-fractionation) are required before food-contact quality hexane is obtained.

The term "sustainable energy" has been used to refer to renewable sources of energy. Biorenewable fuels are a key component of sustainable energy initiatives. Naphtha may be used directly as fuel in industrial furnaces or turbines. It may also be used in small industrial engines such as lawnmowers and chainsaws.

Furthermore, since naphtha hydrocarbons are in the motor gasoline boiling range, they may be used as a gasoline blend stock. Gasoline blends need to meet vapor pressure and octane rating requirements.

One method of producing naphtha hydrocarbons from biomass is by the Fischer-Tropsch (F-T) process. U.S. Pat. No. 7,214,720 to Bayle and co-inventors describes a process involving the steps of (a) gasification, (b) syngas purification, (c) F-T conversion, (d) separation, and (e) recycle of at least a portion of the naphtha to gasifier. Although the process produces the desired hydrocarbon naphtha from a bio-renewable source, gasifiers suffer from a low reliability record. Additionally, the capital costs associated with gasification and F-T conversion are known to be very high. This is in part due to solids handling requirements for the gasifier and heat removal provisions for the highly exothermic F-T reaction. Furthermore, the need to recycle part of the naphtha to the gasifier further reduces the efficiency of this process as a source of bio-renewable naphtha.

U.S. Pat. No. 5,186,722 to Cantrell and Chong describes a catalytic process to convert biomass feeds such as limonene to a composition of cyclic and aromatic compounds in the naphtha boiling range. Although these products are reported to have high octane rating and hence good gasoline blend stocks, they lack the desired properties as a chemical feed stock. As feeds for steam crackers, aromatic compounds give low ethylene and propylene yields. More importantly, the terpene feeds used in the process are among the only biomass sources that to begin with are hydrocarbons. Virtually all other sources of biomass have high oxygen content, typically greater than 10 wt %.

Deoxygenation of biomass feeds such as triglycerides and fatty acids are disclosed in U.S. Pat. No. 7,232,935 to Jakkula and co-inventors. A two step process is disclosed which includes hydrodeoxygenation of triglycerides/fatty acids followed by hydroisomerization. The process produces diesel boiling-range isoparaffins.

To this end, there is a need for biorenewable naphtha that can be used as feed stock for existing petrochemical and refining facilities. In particular, the present invention is a method process for converting high oxygen content biomass, such as sources of triglycerides and/or fatty acids, into naphtha boiling-range hydrocarbons using standard refining processes.

SUMMARY OF THE INVENTION

The present invention relates to a method for producing from a biorenewable feed stock a hydrocarbon naphtha composition useful for producing olefins, BTX aromatics, hydrogen, and also for direct use as gasoline blend stock and solvent. The biorenewable feed stock includes sources of glycerides (i.e. monoglycerides, diglycerides, triglycerides, etc.) and/or fatty acids and combinations thereof, such as animal fats, animal oils, poultry fat, poultry oils, vegetable oils, vegetable fats, plant fats and oils, rendered fats, rendered oils, restaurant grease, brown grease, waste industrial frying oils, fish oils, tall oil, and the like and any combinations thereof.

The method for producing hydrocarbon naphtha includes hydrotreating a renewable feedstock to produce a heavy hydrocarbon fraction. This is followed by hydrocracking of the hydrotreated heavy fraction to produce a distribution of hydrocarbon components, typically $C_3$-$C_{18}$, which is fractionated to recover the naphtha product. The heavy fraction is optionally recycled to the hydrocracker.

The hydrotreating of triglycerides and fatty acids involves olefin hydrogenation and deoxygenation. Hydrotreating thus converts fatty acids into long chain paraffins as illustrated in Equations 1 and 2 for conversion of oleic acid to n-octadecane and n-heptadecane.

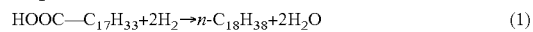

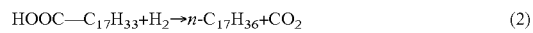

When the fatty acids are supported on a glycerol backbone, for example as triglycerides or diglycerides, the hydrotreating reactions of Equations 1 and 2 produce propane as well as the long chain, heavy hydrocarbon fraction. Depending on the source of the fatty acid/triglyceride, the heavy hydrocarbon fraction is predominantly in the $C_{12}$ to $C_{22}$ range.

The heavy hydrocarbons may be hydrocracked into shorter chain hydrocarbons to produce biorenewable naphtha. In the illustrative hydrocracking reactions of Equations 3-5, n-octadecane is hydrocracked into naphtha-range hydrocarbons, nonanes, hexanes, pentanes, and propane/butanes byproducts.

$$C_{18}H_{38}+H_2 \rightarrow n\text{-}C_9H_{20}+i\text{-}C_9H_{20} \quad (3)$$

$$i\text{-}C_9H_{20}+H_2 \rightarrow i\text{-}C_5H_{12}+C_4H_{10} \quad (4)$$

$$n\text{-}C_9H_{20}+H_2 \rightarrow i\text{-}C_6H_{14}C_3H_8 \quad (5)$$

The naphtha thus obtained is a biorenewable isoparaffinic composition, free of oxygenates and benzene.

The present invention is directed to a naphtha boiling range hydrocarbon composition derived from a biorenewable feedstock. The biorenewable feedstock having monoglycerides, diglycerides, triglycerides, free fatty acids, and combinations thereof. The biorenewable feedstock is selected from the group including animal fats, animal oils, poultry fat, poultry oil, vegetable fats, vegetable oils, rendered fats, rendered oils, restaurant grease, brown grease, waste industrial frying oils, fish oils, fish fats, and combinations thereof. Broadly, the composition of the present invention includes greater than about 90.0% by weight of total n- and iso-paraffins; and less than about 1.0% by weight of total aromatics. The paraffins include $C_4$, $C_5$, $C_6$, $C_7$, $C_8$, $C_9$, and $C_{10}$ paraffins. The composition has a boiling range of about 70° F. to about 400° F. The composition has a specific gravity at 20° C. of from about 0.680 to about 0.740. The composition may further include, less than about 0.5% by weight of olefins, less than about 6.5% by weight of naphthenes, and/or less than about 1.0% by weight of total aromatics.

Further, the present invention is directed to a naphtha boiling range hydrocarbon produced from a biorenewable feedstock, wherein the hydrocarbon has a boiling range between about 70° F. and about 400° F.; and a specific gravity at 20° C. of from about 0.680 to about 0.740. The hydrocarbon has greater than about 90% by weight of total n- and iso-paraffins. The hydrocarbon may further include, less than about 0.5% by weight of olefins, less than about 6.5% by weight of naphthenes, and/or less than about 1.0% by weight of total aromatics. The composition and/or hydrocarbon are free of benzene and oxygenates.

The present invention provides a product produced from a biorenewable feedstock. The product includes a naphtha boiling range hydrocarbon having a boiling range between about 70° F. and about 400° F.; and a specific gravity at 20° C. of from about 0.680 to about 0.740, wherein the product is a benzene-free solvent. The hydrocarbon of the product of the present invention may be fractionated into a bio-based hexane product inherently free of benzene.

DETAILED DESCRIPTION OF THE PREFERRED EMBODIMENTS

The present invention relates to a method for producing from a biorenewable feedstock a hydrocarbon product of naphtha boiling point range that can be used as feedstock for olefins, BTX aromatics, and hydrogen plants. The biorenewable naphtha of the present invention may also be used directly as a fuel, a fuel blend stock, or a solvent.

Figure 1:
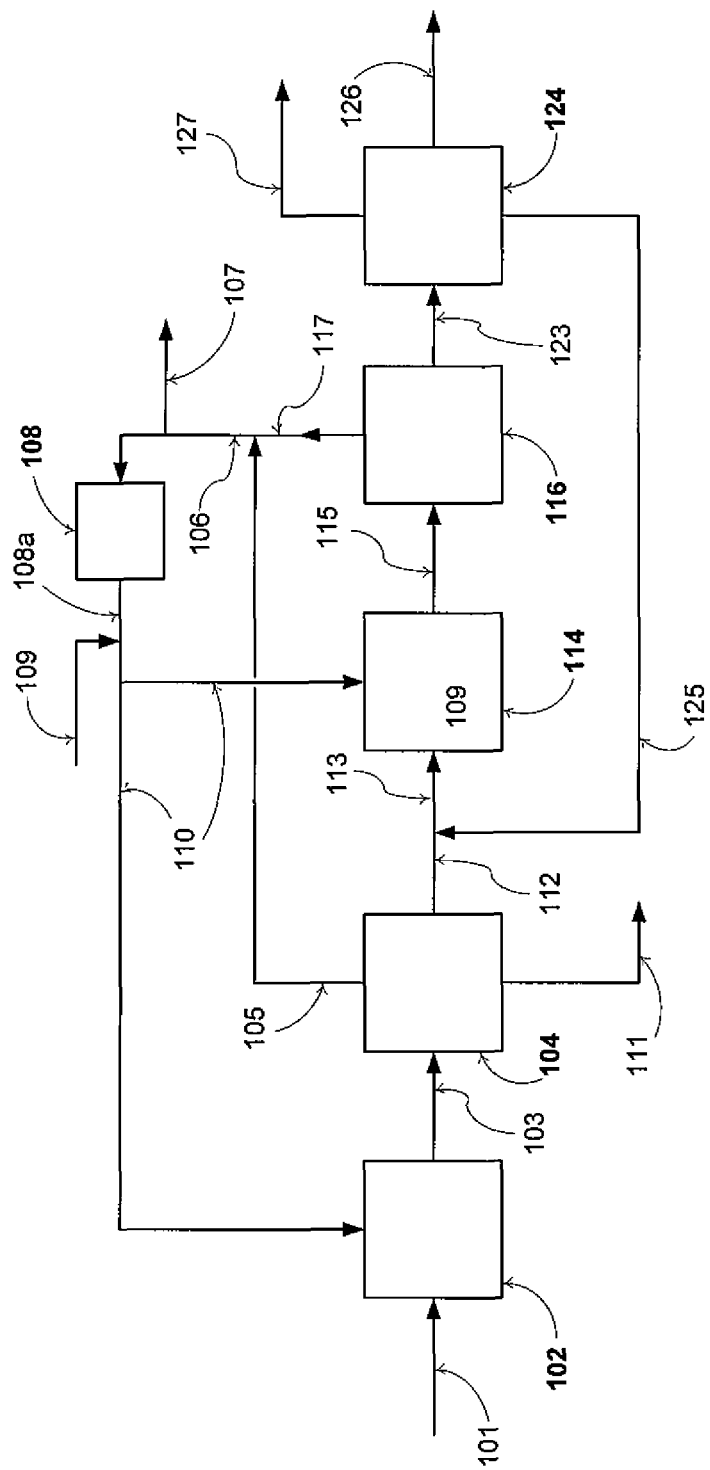
FIG. 1 is a schematic diagram of an operation for producing biorenewable naphtha according to the present invention.

Referring to the process embodiment of FIG. 1, a biorenewable feed 101 is transferred to a hydrotreater 102 where it reacts with hydrogen under pressure of from about 300 psig to about 3,000 psig, preferably from about 1,000 psig to about 2,000 psig. Feed 101 may optionally be pretreated to remove contaminants. The hydrotreater 102 is preferably a packed bed of sulfided bimetallic catalyst, preferably nickel-molybdenum (NiMo), nickel-tungsten (NM), or cobalt-molybdenum (CoMo) on alumina support. It should be understood by one of ordinary skill in the art that any catalyst may be used in the present invention so long as the catalyst functions in accordance with the present invention as described herein.

To maintain the active metal sulfide functionality of the catalyst despite absence of organic sulfur in most bio-renewable feeds, feed 101 may be supplemented with a sulfur compound that decomposes to hydrogen sulfide when heated and/or contacted with a catalyst. Two preferred sulfur compounds are dimethyl disulfide and carbon disulfide. Preferred concentration of these in the feed 101 is from about 100 to about 2,000 ppm by weight sulfur. Alternatively, feed 101 may include a biorenewable component and a petroleum fraction wherein the petroleum-fraction provides the sulfur.

Feed 101 may be preheated before entering the hydrotreater 102. The hydrotreater 102 operates from about 300° F. to about 900° F., preferably from about 550° F. to about 650° F., and from about 250 psig to about 3,000 psig. In order to reduce the adiabatic temperature rise from the exothermic hydrotreating reactions and to maintain the hydrotreater 102 in the preferred operating range, a number of methods known in the art may be used. These methods include, but are not limited to, feed dilution with a solvent or other diluent, liquid product or solvent recycle, and use of quench zones within the fixed-bed reactor wherein hydrogen is introduced.

The biorenewable feed 101 liquid hourly space velocity through the hydrotreater 102 is from about $0.2 \text{ h}^{-1}$ to about $10 \text{ h}^{-1}$, preferably from about $0.5 \text{ h}^{-1}$ to about $5.0 \text{ h}^{-1}$. The ratio of hydrogen-rich treat gas 110 to biorenewable feed 101 is preferably in the about 2,000 to about 15,000 SCF/bbl range. The hydrogen-rich treat gas 110 may contain from about 70 mol % to about 100 mol % hydrogen.

A hydrotreater effluent 103 includes a deoxygenated heavy hydrotreater fraction and unreacted hydrogen. The hydrotreater effluent 103 may also include water, carbon oxides, ammonia, and hydrogen sulfide. The long chain, heavy hydrocarbon fraction in the liquid phase is separated from the gas phase components in a separation unit 104.

The separation unit 104 includes a high pressure drum (not shown) operated at hydrotreater discharge pressure (about 1,000 psig to about 2,000 psig in the preferred embodiment), wherein long chain, heavy hydrocarbon liquids are separated from hydrogen and gas phase hydrotreater byproducts. It should be understood that the hydrotreater discharge pressure may be operated from about 200 psig to about 3,000 psig. Depending on the temperature of the separation unit 104, water may be in vapor or liquid phase. In a preferred embodiment, the separation unit 104 has a temperature in the about 350° F. to about 500° F. range whereby water, carbon oxides, ammonia, hydrogen sulfide, and propane are removed with hydrogen in a separator drum vapor phase. To enhance removal of the components from the heavy hydrocarbon fraction, the separation unit 104 optionally includes a stripping section (not shown). Water 111 may be condensed, separated, and the hydrogen-rich gas phase 105 recycled to the hydrotreater 102.

A long chain hydrocarbon product stream 112 from the separation unit 104 is then cracked in a hydrocracker 114. Product stream 112 is optionally combined with unconverted heavies from the hydrocracker 114, and recycled stream 125, to form a hydrocracker feed 113.

The heavy hydrocarbon feed 113 cracks in the hydrocracker 114 to form naphtha-range hydrocarbons. Preferably, the hydrocracker 114 operates from about 250 psig to about 3,000 psig, more preferably from about 1,000 psig to about 2,000 psig. Hydrocracker 114 temperatures are from about 400° F. to about 900° F., preferably from about 580° F. to about 750° F. Suitable catalysts for hydrocracking according to the present invention as described herein are bi-functional catalysts with hydrogenation and acidic functionalities. Such catalysts include Group VIII metals on amorphous (e.g. silica-alumina) or crystalline (e.g. zeolite) supports. Preferred hydrocracking catalysts are platinum, palladium or combinations of same on an amorphous silica-alumina support. However, it should be understood that any catalyst may be used in accordance with the present invention as long as it functions as described herein. Preferred ratios of the hydrogen-rich gas to liquid feed for hydrocracking are in the about 1,000 to about 10,000 SCF/bbl range, and liquid hourly space velocity in the about 0.1 $h^{-1}$ to about 8 $h^{-1}$ range, preferably from about 0.2 $h^{-1}$ to about 4 $h^{-1}$. Stream 115 is an effluent of the hydrocracker 114 wherein un-reacted hydrogen includes a gas phase. Hydrogen-rich gas is separated from the hydrocarbon product in a separation unit 116.

The separation unit 116 includes a high pressure separation drum (not shown), operating at hydrocracker discharge pressure, about 1,000 psig to about 2,000 psig in the preferred embodiment, where hydrocarbon liquids are separated from hydrogen, hydrocarbon vapors, and any other gas phase cracked products. It should be understood that the hydrocracker discharge pressure may be operated from about 200 psig to about 3,000 psig.

A hydrogen-rich gas 117 from the separation unit 116 is combined with a hydrogen-rich gas 105 from the separation unit 104 and optionally processed through an absorption column or scrubber 108 to remove ammonia, carbon oxides, and/or hydrogen sulfide, before recompression for recycle to the hydrotreater 102 and/or hydrocracker 114. Depending on the contaminant to be removed, the scrubber 108 may use various solvents such as amine and caustic solutions. It is clear to those skilled in the art that other gas cleanup technologies may be used instead of or in addition to the scrubber 108 to remove contaminants that affect the hydrotreater 102 and hydrocracker 114 catalyst activity and selectivity. Examples of alternative gas cleanup technologies include membrane systems and adsorbent beds.

A purge stream 107 may be removed from a recycle gas 106 to prevent buildup of contaminants that are not effectively removed in the scrubber 108. The cleaned hydrogen-rich gas 108a from the scrubber 108 may be combined with makeup hydrogen 109 to form a hydrogen-rich gas stream 110 for the hydrotreater 102 and hydrocracker 114.

Stream 123 is the liquid hydrocarbon phase from the separation unit 116. Stream 123 is processed through fractionator unit 124 to fraction the hydrocracker products into a hydrocarbon vapors product 127, the desired naphtha product 126, and a heavies fraction 125 which is optionally recycled to extinction through the hydrocracker 114.

The fractionator unit 124 is operated to recover biorenewable naphtha, typically with a $C_4$-$C_9$ hydrocarbon distribution. Despite the relatively high oxygen content of the biological feedstock, the naphtha product is free of oxygenates. The biorenewable naphtha includes 80% to 100% by weight n- and iso-paraffins. In preferred embodiments of this invention, biorenewable naphtha n- and iso-paraffin content is greater than 90% by weight. The total aromatics content is in the range of 0 to 2% by weight, preferably less than 1% by weight. Cycloparaffins (or naphthenes as they are more commonly known) may also be present in the biorenewable naphtha at up to 7.0% by weight. The olefin content of biorenewable naphtha is less than 0.5% by weight, preferably in the range of 0 to 0.3% by weight.

No benzene is present in the biorenewable naphtha. The biorenewable naphtha product may thus be used as a solvent for food-contact applications. For example, stream 126 may be subjected to conventional distillation for separating the $C_6$-cut from the $C_4$-$C_{10}$ paraffinic hydrocarbon distribution, wherein the $C_6$-cut is used as bio-based hexane solvent for vegetable oil extraction.

Figure 2:
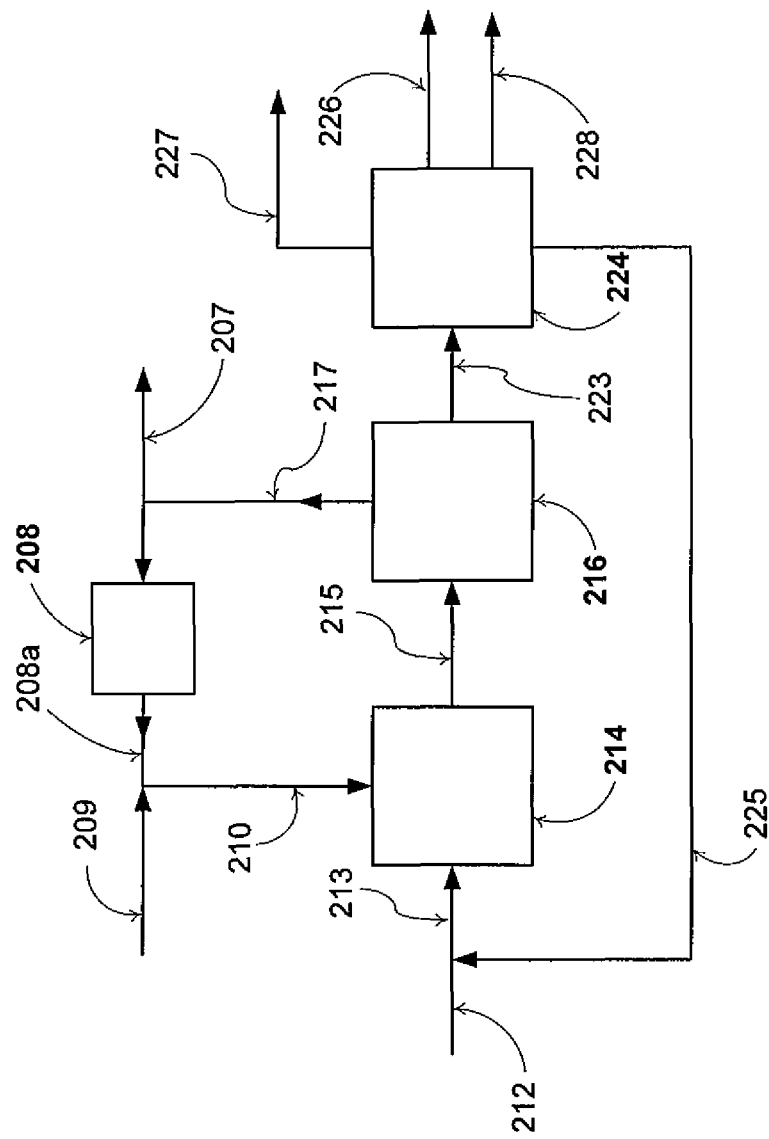
FIG. 2 is a schematic diagram of another embodiment of a method for producing biorenewable naphtha in accordance with the present invention.

Referring now to FIG. 2, another embodiment of the present invention is illustrated. A biorenewable feed enters a hydrotreater reactor (not shown). Stream 212 is the heavy hydrocarbon product of the hydrotreating reaction in the hydrotreater. Stream 212 is optionally combined with an unconverted heavy fraction 225 to form a hydrocracker feed 213. Hydrocracker feed 213, a $C_{15}$-$C_{22}$ hydrocarbon distribution for most common triglycerides and fatty acids, is converted to a $C_3$-$C_{18}$ distribution in a hydrocracker 214. An effluent 215 from the hydrocracker 214, is separated into a hydrogen-rich gas stream 217 and a cracked liquids stream 223 in a separation unit 216. Operating conditions are the same as for FIG. 1.

A fraction of the hydrogen-rich gas 217 is purged as stream 207 and the remaining fraction of the hydrogen-rich gas 217 is cleaned up in scrubber 208. The cleaned hydrogen-rich gas 208a is then combined with makeup hydrogen 209 to form a recycle hydrogen-rich gas as hydrocracker stream 210.

Stream 223, cracked liquids from the separation unit 216, is transferred to a product fractionators unit 224. The illustrative $C_3$-$C_{18}$ hydrocracked product is fractioned into a $C_3$/$C_4$ gas stream 227, a naphtha product stream 226, a middle distillate stream 228 suitable for use as jet kerosene or diesel, and a heavies recycle stream 225.

The resultant biorenewable naphtha has a boiling point range from about 70° F. to about 400° F. and a specific gravity at 20° C. of from about 0.680 to about 0.740. The naphtha product includes $C_4$-$C_{10}$ paraffins that are considered superior feed components for steam crackers, and is also an appropriate feed for conversion to BTX aromatics, and hydrogen production. The naphtha composition is also useful as a solvent in applications where low flash point is not a limitation.

As a fuel or fuel additive, the renewable naphtha provides some benefit as a bio-renewable addition to ethanol in that ethanol typically suffers from low vapor pressures and low energy density. The biorenewable naphtha typically has a Reid Vapor Pressure (RVP)>10 psi and may be blended with ethanol in concentrations of 1-30% to make an entirely renewable gasoline replacement for automobiles that has an improved energy density. The bio-renewable naphtha has low octane ratings (typically less than 40 RON) which is offset by the higher octane of the ethanol fuel which is reported to be in the 129 RON range. Thus, the resulting blend easily meets U.S. performance requirements for vapor pressure and octane rating by utilizing the benefits of both fuels.

An alternate approach for using the biorenewable naphtha of the present invention as described herein as a renewable blend stock for motor gasoline is by isomerization of the $C_5/C_6$ fraction, which is a standard refinery unit process. The $C_5/C_6$ fraction of the biorenewable naphtha composition may be isomerized to raise RON and make it suitable for blending with gasoline stocks. Typical isomerized products include 2-methylbutane and 2,3-dimethylbutane, with RON values of 93.5 and 105, respectively.

The biorenewable naphtha is used as fuel for industrial burners, boilers, and turbines and as an industrial solvent.

Due to its paraffinic nature and its high hydrogen-to-carbon ratio, the bio-renewable naphtha may also be used as a hydrogen source or as a fuel cell fuel.

In order to further illustrate the present invention, the following examples are given. However, it is to be understood that the examples are for illustrative purposes, only and are not to be construed as limiting the scope of the subject invention.

EXAMPLES

Example 1

Hydrotreating of a Biorenewable Feed Stock

The present example demonstrates how naphtha was made from a renewable feedstock. A 100 cc isothermal tubular reactor was filled with 80 cc of a commercial NiMo catalyst and +70-100 mesh glass beads. The catalyst was suifided with dimethyl disulfide. The sulfiding procedure included stepwise temperature increase to 650° F. After sulfiding, the reactor was cooled to 400° F.

Next a triglyceride/fatty acid feed was introduced to the isothermal reactor. The reactor was slowly heated to 650° F. to achieve full conversion of the triglyceride/fatty acid feed to n-paraffins. The reactor temperature was further increased to 700° F. to maintain good catalyst activity at 80 cc/hr feed rate (1 LHSV).

The hydrotreater performance with beef tallow as the triglyceride/fatty acid feed is summarized in Table 1. The yield of total products on feed basis exceeds 100% in part due to addition of hydrogen and also due to measurement errors associated with gas phase analysis.

TABLE 1

Hydrotreater Conditions and Conversion Performance.

| Catalyst | |
|---|---|
| Active Metals | Sulfided NiMo |
| Support | Alumina |
| Reactor Conditions | |
| Feed | Inedible tallow |
| Temperature (° F.) | 700 |
| Pressure (psig) | 1,200 |
| Gas/Oil Ratio (scf/bbl) | 14,000 |
| LHSV | 1 |
| Products (wt % feed basis) | |
| C1 + C2 | 1.5 |
| Propane | 6.1 |
| Water | 5.3 |
| Total Liquid Hydrocarbons | 88.2 |

Figure 3:
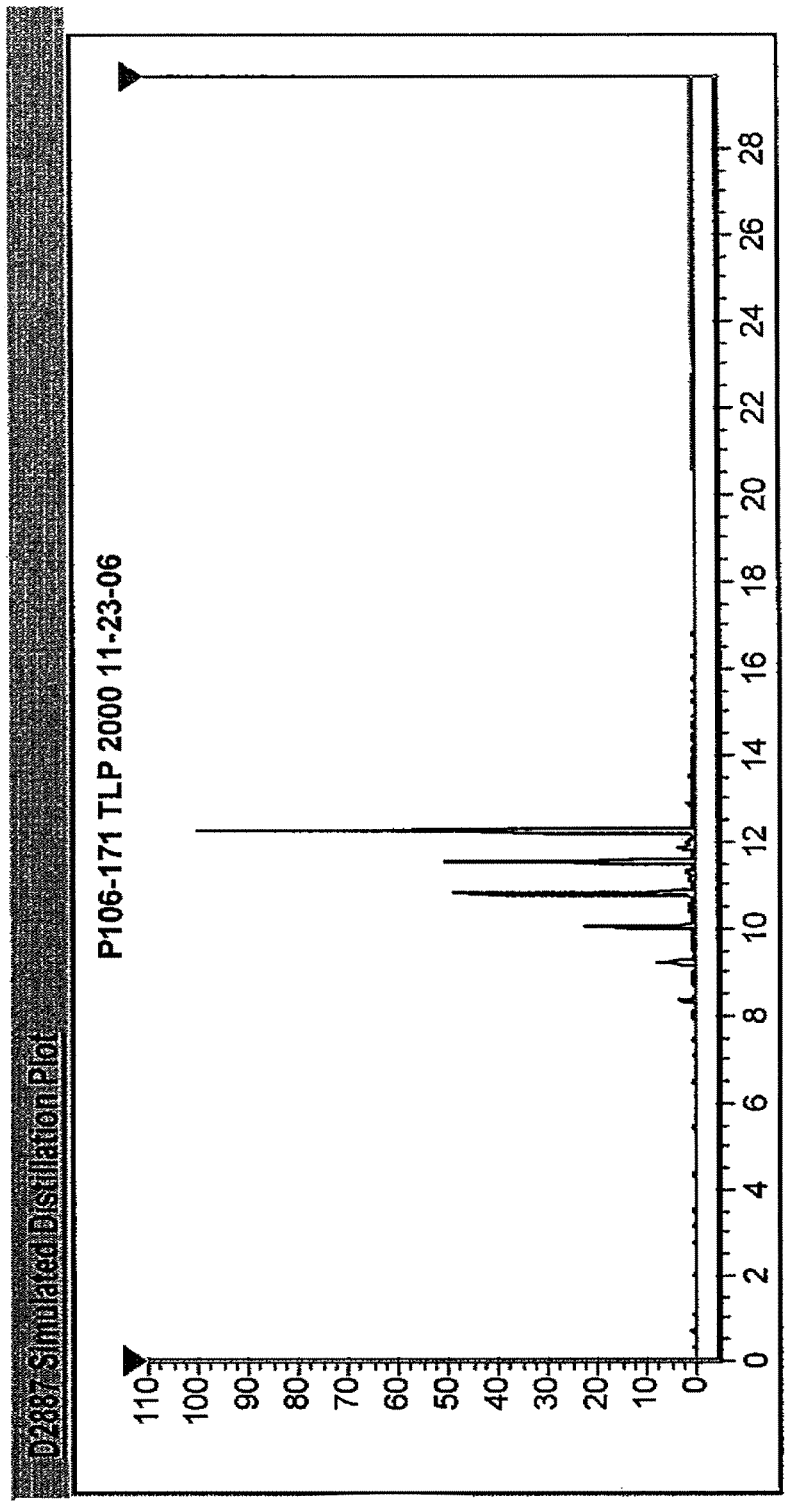
FIG. 3 is a gas chromatogram showing product from an example.

The gas chromatogram of the liquid hydrocarbon product confirmed that under the hydrotreater conditions of Table 1 the tallow feed was converted $C_{15}$-$C_{18}$ n-paraffins with no detectable oxygenates remaining. No cracked products ($C_{12}$—) were detected. FIG. 3 is the chromatogram of the product, showing areas where cracked products and unconverted feed would appear.

Example 2

Hydrocracking of Bio-Derived Heavy Hydrocarbons

The mainly $C_{15}$-$C_{18}$ n-paraffin composition obtained from hydrotreating bio-renewable feed stocks was used as feed for a hydrocracking pilot plant. These long chain hydrocarbons were derived via hydrotreating a biorenewable feed in a procedure similar to Example 1. The bio-renewable feed was a blend of chicken fat (45%), brown grease (19%), yellow grease (18%), floatation grease (9%), and miscellaneous waste animal fats from industrial food processing operations (9%). The hydrocracking pilot plant was a prototype of the embodiment of the present invention represented by FIG. 2.

The hydrocracker reactor system was loaded with 4.8 liters of a commercial hydrocracking catalyst. The catalyst was platinum-palladium on amorphous alumina/silica support. The reactor was pressurized to 1,000 psig. After catalyst preconditioning, the temperature was increased again to achieve the desired level of hydrocracking to produce the biorenewable naphtha product. The ratio of hydrogen-rich gas (recycle and makeup) to feed was 3,600-3,800 SCF/bbl.

The pilot plant fractionation system included three distillation columns in series. The first stripped off the light hydrocarbons ("debutanizer") from the hydrocracker effluent, the second ("naphtha tower") separated the naphtha overhead, and the third ("recycle tower") separated a middle distillate cut overhead from the heavy bottoms that were combined with the fresh feed and recycled to the hydrocracker.

Table 2 provides the composition and properties of the hydrotreated hydrocarbon fraction and Table 3 summarizes the operating conditions of the hydrocracker, conversion performance thereof, and product properties therefrom.

TABLE 2

Composition and properties of hydrocracker feed of Example 2[a]

| Component | Normal Boiling Pt. (° F.) | Example 2 Feed | ASTM D2887SimDist (° F.) | |
|---|---|---|---|---|
| C10 | 345 | ND | IBP | 345 |
| C11 | 385 | ND | 5% | 516 |
| C12 | 421 | ND | 10% | 543 |
| C13 | 455 | ND | 20% | 549 |
| C14 | 489 | 1.55 | 30% | 550 |
| C15 | 520 | 1.93 | 40% | 576 |
| C16 | 549 | 26.03 | 50% | 599 |
| C17 | 576 | 4.86 | 60% | 599 |
| C18 | 601 | 64.36 | 70% | 601 |
| C19 | 626 | 0.00 | 80% | 601 |
| C20 | 651 | 1.27 | 90% | 603 |
| C22 | 696 | ND | 95% | 604 |
| total paraffins | | 100.0 | FBP | 671 |

[a]ND = not detectable

TABLE 3

Hydrocracker Run Conditions, Conversion Performance, and Product Properties [a]

| Reactor Conditions | |
|---|---|
| Reactor 1 Temp (° F.) | 726 |
| Reactor 2 Temp (° F.) | 721 |
| Pressure (psig) | 1002 |
| Feed Rates | |
| Fresh Feed Wt (g/hr) | 2241.0 |
| Fresh Feed Vol (cc/hr) | 2817.5 |
| Recycle Feed Wt (g/hr) | 807.6 |
| Recycle Feed Vol (cc/hr) | 1026 |
| Total Feed Vol (cc/hr) | 3843 |
| LHSV | 0.794 |
| Gas Rates | |
| $H_2$ Makeup (scf/hr) | 24.5 |
| Inlet Gas (scf/hr) | 102.2 |
| Bleed Gas (scf/hr) | 15.5 |
| Product Rates | |
| C3/C4 (g/hr) | |
| Non-condensed C5–C6+ (g/hr) | |
| Naphtha (g/hr) | 561.3 |
| Middle Distillate Ovhd (g/hr) | 1536.5 |
| Naphtha Yields | |
| Non-condensed C5–C6 (wt %) | 3.3% |
| Condensed naphtha (wt %) | 25.0% |
| Total naphtha (wt %) | 28.3% |
| Material Balance Closure | 100.1% |
| Naphtha Tower Temps | |
| Reboiler Liquid | 336 |
| Column Skin | 409 |
| Column Top | 293 |
| Preheater | 303 |
| Recycle Tower Temp | |
| Reboiler Liquid | 564 |
| Column Skin | 534 |
| Column Top | 492 |
| Preheater | 499 |
| Recycle heavies spec. grav. | 0.787 |
| Naphtha Properties | |
| Specific Gravity | 0.705 |
| D2887 SimDist (° F.) | |
| IBP | 70 |
| 5 | 91 |
| 10 | 135 |
| 20 | 159 |
| 30 | 194 |
| 40 | 211 |
| 50 | 244 |
| 60 | 260 |
| 70 | 290 |
| 80 | 318 |
| 90 | 358 |
| 95 | 387 |
| FBP | 432 |
| Middle Distillate Properties | |
| API | 51.5 |
| Specific Gravity | 0.773 |
| Freeze Point (oC) | −39.5 |
| Cloud Point (° C.) | −43.0 |
| Flash Point (° F.) | 126 |
| D2887 SimDist (° F.) | |
| IBP | 226 |
| 5 | 291 |
| 10 | 330 |
| 20 | 374 |
| 30 | 412 |
| 40 | 446 |
| 50 | 479 |
| 60 | 510 |
| 70 | 526 |
| 80 | 544 |
| 90 | 565 |
| 95 | 575 |
| FBP | 593 |

[a] NM = not measured

Example 3

Bio-Renewable Naphtha as Blendstock for 100% Renewable E-85 Gasoline

Fuel grade bio-ethanol was purchased from Abengoa Bioenergy (Chesterfield, Mo.). The biorenewable naphtha was produced using the Conditions of Examples 1 and 2 with the feedstock of Example 2. Using these blendstocks, an 85 vol % ethanol blend with the bio-renewable naphtha was prepared. Test aliquots of this 100% renewable E-85 gasoline were taken according to ASTM D 2699 and ASTM D 2700 test methods, and Research and Motor Octane Numbers (RON and MON) were measured. The results are summarized in Table 4.

TABLE 4

Octane Rating of 100% Renewable E-85 Gasoline

| Test Method | Test Description | Results |
|---|---|---|
| ASTM D 2699 | RON | 101.6 |
| ASTM D 2700 | MON | 89.6 |
| Anti-knock Index | (R + M)/2 | 95.6 |

The results of Table 4 indicate that the bio-renewable naphtha composition of this invention is well-suited for producing a high octane, 100% renewable gasoline, containing virtually no aromatic hydrocarbons.

Example 4

Steam Cracking of Bio-Renewable Naphtha

A pilot plant steam cracker designed to model performance of commercial units (Van Geem, K. M.; Reyniers, M.-F.; Marin G. B. AIChE J., 50, 173-183, 2004) was used for this experiment. The experiments were conducted using the biorenewable naphtha composition of this invention produced according to the method of Examples 1 and 2. The steam cracker coil outlet pressure was controlled at 1.7 bar, with steam-to-hydrocarbon ratio of 0.45 w/w. The yields of the bio-derived olefins for selected coil outlet temperature (COT) experiments are presented in Table 5. Also included in Table 5 is comparable data for petroleum distillates of similar boiling range.

TABLE 5

Product yields from steam cracking of biorenewable naphtha and petroleum feedstocks of similar boiling range

| Feedstock | Medium Range Petroleum Naphtha[a] | Atm. Gas oil (petroleum)[a] | Biorenewable naphtha-COT = 1,562° F. | Biorenewable naphtha-COT = 1,535° F. |
|---|---|---|---|---|
| | Cracking Yield | | | |
| Hydrogen and methane | 17.7 | 12.1 | 17.32 | 16.03 |
| Ethylene | 34.0 | 25.9 | 30.92 | 30.13 |
| Propylene | 15.7 | 16.2 | 17.59 | 18.94 |
| Butadiene | 4.7 | 4.6 | 5.165 | 5.282 |
| Total $C_4^-$ products | 76.4 | 63.6 | 84.04 | 85.0 |
| Pyrolysis gasoline | 18.8 | 18.4 | 14.79 | 14.65 |
| Pyrolysis fuel oil | 4.8 | 18.0 | 0.438 | 0.359 |
| Total | 100.0 | 100.0 | 99.3 | 100.0 |

[a]Petroleum steam cracking data from Grub J. and Loser, E. Ullmann's Encyclopedia of Indusrial Chemistry, John Wiley; 2005.

As observed in Table 5, the biorenewable naphtha cracks more completely to light olefins than do petroleum feedstocks (higher $C_4$-products and lower pyrolysis liquids). Yields of the main olefins (ethylene, propylene, and butadiene) are also generally similar or better than petroleum feeds of similar boiling range.

Example 5

Composition of Renewable Naphtha

A sample of the naphtha boiling range product produced in Example 2 was submitted for detailed characterization via GCxGC. This analytical technique, also referred to as "two dimensional GC," is used for quantitative analysis of complex mixtures. The technique uses two chromatography columns—with a modulator in between—to separate the components based on volatility (x-axis) and polarity (y-axis), thus generating a two-dimensional map of the product composition. As such, compounds with similar volatility but slightly different polarity can be quantified independently (e.g. pentane and methyl-cyclobutane, both having a 36° C. boiling point).

TABLE 6

Composition (wt %) of Bio-Renewable Naphtha Produced in Example 2.

| Carbon Number | Paraffin | Iso-Paraffin | Olefin | Naphthene (Cycloparaffin) | Aromatic | Sum |
|---|---|---|---|---|---|---|
| 3 | 0.172 | 0.000 | 0.000 | 0.000 | 0.000 | 0.172 |
| 4 | 1.506 | 0.963 | 0.000 | 0.000 | 0.000 | 2.468 |
| 5 | 4.584 | 4.956 | 0.000 | 0.000 | 0.000 | 9.540 |
| 6 | 7.784 | 9.946 | 0.000 | 1.055 | 0.000 | 18.784 |
| 7 | 7.964 | 12.870 | 0.000 | 1.389 | 0.108 | 22.331 |
| 8 | 5.598 | 11.140 | 0.022 | 1.708 | 0.305 | 18.773 |
| 9 | 3.249 | 10.745 | 0.255 | 1.708 | 0.331 | 16.289 |
| 10 | 1.237 | 6.519 | 0.061 | 0.622 | 0.089 | 8.528 |
| 11 | 0.251 | 2.172 | 0.000 | 0.046 | 0.000 | 2.469 |
| 12 | 0.062 | 0.581 | 0.000 | 0.000 | 0.000 | 0.644 |
| SUM | 32.407 | 59.893 | 0.338 | 6.528 | 0.833 | 100 |

The GCxGC analysis, summarized in Table 6, confirms that the renewable naphtha product of the instant invention is paraffinic, with total of only 0.338 wt % olefins and 0.833 wt % aromatics. Furthermore, no benzene (0.00% $C_6$ aromatics) was observed. Absence of carcinogenic benzene and very low aromatics content makes this biorenewable composition inherently less toxic than petroleum-based naphtha.

Example 6

A naphtha distillate was produced via hydrotreating of beef tallow according to the process of the instant invention. The naphtha distillate was submitted for analysis at a certified ASTM testing laboratory. The measured properties are summarized in Tables 7a and 7b below.

TABLE 7a

PIONA and oxygenates analysis of biorenewable naphtha (wt %)

| Carbon No. | Paraffins | Iso-Paraffins | Olefins | Naphthenes | Aromatics | Oxygenates | Total |
|---|---|---|---|---|---|---|---|
| 3 | 0.882 | 0.000 | 0.000 | 0.000 | 0.000 | 0.000 | 0.882 |
| 4 | 1.207 | 0.962 | 0.000 | 0.000 | 0.000 | 0.000 | 2.169 |
| 5 | 4.242 | 5.985 | 0.000 | 0.050 | 0.000 | 0.000 | 10.277 |
| 6 | 6.867 | 11.773 | 0.000 | 0.784 | 0.000 | 0.000 | 19.423 |
| 7 | 6.629 | 14.537 | 0.000 | 1.629 | 0.000 | 0.000 | 22.795 |
| 8 | 5.457 | 14.673 | 0.000 | 2.364 | 0.344 | 0.000 | 22.838 |
| 9 | 3.518 | 12.691 | 0.000 | 0.693 | 0.714 | 0.000 | 17.616 |
| 10 | 0.412 | 3.588 | 0.000 | 0.000 | 0.000 | 0.000 | 4.000 |
| Total | 29.214 | 64.209 | 0.000 | 5.519 | 1.058 | 0.000 | 100.0 |

TABLE 7b

Physical properties of renewable naphtha

| Property | Test Result |
|---|---|
| Relative Density | 0.683 |
| Reid Vapor Pressure (psi) at 100° F. | 7.606 |
| Calculated Octane Number | 58.06 |
| Boiling Range (° F.) | |
| IBP | −43.67 |
| 10 vol % | 96.91 |
| 50 vol % | 200.25 |
| 90 vol % | 291.61 |
| FBP | 345.47 |

TABLE 7b-continued

Physical properties of renewable naphtha

| Property | Test Result |
| --- | --- |
| Percent Carbon | 84.04 |
| Percent Hydrogen | 15.96 |
| Nitrogen (wppm) | Below detection (<0.3) |
| Chloride (wppm) | Below detection (<1) |
| $H_2S$ content (wppm) | Below detection (<1) |

Thus, there has been shown and described a method for producing a biorenewable naphtha product that fulfills all objectives and advantages sought therefore. While presently preferred embodiments of the invention have been described for purposes of this disclosure, it will be understood that numerous changes may be made which will readily suggest themselves to those skilled in the art and which are accomplished within the spirit of the invention disclosed and claimed herein. From the above description, it is clear that the present invention is well adapted to carry out the objects and to obtain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and claimed.

What is claimed is:

1. A naphtha boiling range hydrocarbon composition comprising:
    n-paraffins, iso-paraffins, aromatics, and naphthenes;
    wherein the composition
        is produced by hydrocracking a hydrotreated biorenewable feedstock;
        comprises
            $C_4$, $C_5$, $C_6$, $C_7$, $C_8$, and $C_9$ hydrocarbons;
            greater than 80.0% by weight n- and iso-paraffins; and
        is free of benzene.

2. The composition of claim 1, wherein the composition has a specific gravity at 20° C. of 0.680 to 0.740.

3. The composition of claim 1, wherein the n-paraffins and iso-paraffins both comprise $C_4$, $C_5$, $C_6$, $C_7$, $C_8$, $C_9$, and $C_{10}$ paraffins.

4. The composition of claim 1, wherein the biorenewable feedstock comprises monoglycerides, diglycerides, triglycerides, free fatty acids, or combinations thereof.

5. The composition of claim 4, wherein the biorenewable feedstock is selected from the group comprising animal fats, animal oils, poultry fat, poultry oil, vegetable fats, vegetable oils, rendered fats, rendered oils, restaurant grease, brown grease, waste industrial frying oils, fish oils, fish fats, and combinations thereof.

6. The composition of claim 1, comprising greater than 90% by weight n- and iso-paraffins.

7. The composition of claim 1, comprising less than 0.5% by weight olefins.

8. The composition of claim 1, comprising less than 0.3% by weight olefins.

9. The composition-of claim 1, comprising less than 7.0% by weight naphthenes.

10. The composition of claim 1, comprising less than 6.5% by weight naphthenes.

11. The composition of claim 1, comprising less than 2% by weight total aromatics.

12. The composition of claim 1, comprising less than 1.0% by weight total aromatics.

13. The composition of claim 1, wherein the composition is free of oxygenates.

14. The composition of claim 1, comprising:
    greater than 90.0% by weight n- and iso-paraffins;
    less than 0.5% by weight olefins;
    less than 7.0% by weight naphthenes; and
    less than 2% by weight total aromatics.

15. The composition of claim 1, comprising:
    greater than 90.0% by weight n- and iso-paraffins;
    less than 0.5% by weight olefins;
    less than 7.0% by weight naphthenes;
    less than 2% by weight total aromatics; and
    wherein the composition is free of oxygentates.

16. The composition of claim 1, comprising:
    greater than 90.0% by weight n- and iso-paraffins;
    less than 0.3% by weight olefins;
    less than 6.5% by weight naphthenes; and
    less than 2% by weight total aromatics.

17. The composition of claim 1, comprising:
    greater than 90.0% by weight n- and iso-paraffins;
    less than 0.3% by weight olefins;
    less than 6.5% by weight naphthenes; and
    less than 1.0% by weight total aromatics.

18. A naphtha boiling range hydrocarbon composition, comprising:
    n-paraffins, iso-paraffins, aromatics, and naphthenes;
        wherein the composition comprises
            $C_4$, $C_5$, $C_6$, $C_7$, $C_8$, and $C_9$ hydrocarbons;
            greater than 90.0% by weight n- and iso-paraffins;
            less than 0.3% by weight olefins;
            less than 7.0% by weight naphthenes;
            less than 2% by weight total aromatics; and
            is free of benzene and oxygenates.

19. The composition of claim 18, wherein the n-paraffins and iso-paraffins both comprise $C_4$, $C_5$, $C_6$, $C_7$, $C_8$, $C_9$, and $C_{10}$ paraffins.

* * * * *